United States Patent [19]
Grollier et al.

[11] Patent Number: 4,888,164
[45] Date of Patent: Dec. 19, 1989

[54] COSMETIC COMPOSITION FOR THE TREATMENT OF OILY SKIN AND HAIR BASED ON DI(BETA-HYDROXYETHYL) SULFOXIDE AND THE USE THEREOF

[75] Inventors: Jean-Francois Grollier, Paris; Jean Maignan, Tremblay Les Gonesse, both of France

[73] Assignee: L'Oreal, Paris, France

[21] Appl. No.: 944,166

[22] Filed: Dec. 22, 1986

[30] Foreign Application Priority Data

Dec. 27, 1985 [LU] Luxembourg ............................ 86229

[51] Int. Cl.$^4$ .......................... A61K 7/48; A61K 7/06; A61K 7/075
[52] U.S. Cl. ........................................ 424/63; 424/70; 424/71; 514/772; 252/DIG. 13
[58] Field of Search ............... 568/27; 514/772, 227.5, 514/708, 738; 424/70, 71, DIG. 2, 47; 252/DIG. 13

[56] References Cited

U.S. PATENT DOCUMENTS

| | | | |
|---|---|---|---|
| 3,950,532 | 4/1976 | Bouillon et al. | 424/71 X |
| 4,080,465 | 3/1978 | Bouillon et al. | 424/71 X |
| 4,108,866 | 8/1978 | Tramier et al. | 568/27 X |

FOREIGN PATENT DOCUMENTS 1125409  8/1968  United Kingdom .

*Primary Examiner*—Thurman K. Page
*Assistant Examiner*—Susan S. Rucker
*Attorney, Agent, or Firm*—Cushman, Darby & Cushman

[57] ABSTRACT

A cosmetic composition to combat the oily appearance of the hair and skin contains, as the active component, di($\beta$-hydroxyethyl)sulfoxide. A process for treating the hair or skin to improve the appearance thereof is also disclosed.

1 Claim, No Drawings

COSMETIC COMPOSITION FOR THE TREATMENT OF OILY SKIN AND HAIR BASED ON DI(BETA-HYDROXYETHYL) SULFOXIDE AND THE USE THEREOF

The present invention relates to new cosmetic compositions intended for the treatment of oily skin and hair, said compositions being based on di($\beta$-hydroxyethyl)sulfoxide, and to their use.

It is known that a significant number of individuals suffer from an oily and unesthetic appearance of the skin and hair. The oily appearance is due to an excessive secretion of sebum by the sebaceous glands.

There has already been proposed, to suppress the oily and unesthetic appearance of the scalp and skin, cosmetic compositions based on certain sulfur derivatives such as, for example, S-substituted derivatives of cysteine or cysteamine or certain homologs of these compounds, or based on derivatives of thiolannediol; see for example French Patent No. 72.16948.

It has now been discovered that di($\beta$-hydroxyethyl) sulfoxide exhibits interesting properties permitting their use to combat the oily appearance of the hair and skin. Contrary to certain compounds whose use has been previously recognized, this sulfoxide provides the advantage of not charging the hair, even in the case of repeated use, of not modifying the other cosmetic properties of formulations (neutrality) and of being more easily combined with other additives (compatibility).

The di($\beta$-hydroxyethyl) sulfoxide is a known compound which is described, for example, in French Patent Application No. 73.37867 (Publication No. 2.249.077). This French patent application describes the preparation of di($\beta$-hydroxethyl sulfoxide and analogous compounds by a method comprising oxidizing the corresponding thiodialcohol with $H_2O_2$ either in an aqueous medium in the presence of acetic acid, or in a solvent capable of forming an azeotrope with water such as, for example, a heptane-water mixture in the presence of a catalytic amount of acetic acid or another organic acid capable of generating a peracid under the action of $H_2O_2$.

French Patent Application 73.37867 describes the use of the organic sulfoxides as thickening agents in oily compositions, paints or cosmetics. This French patent application does not, however, describe cosmetic compositions containing di($\beta$-hydroxyethyl) sulfoxide.

In Belgian Patent No. 684,960 there is described the pharmaceutical use of, as antiinflammatory agents and as tissue penetration agents, certain hydroxy-hydrocarbon sulfoxides.

The present invention has for an object new cosmetic compositions intended to combat the oily appearance of the scalp and skin, characterized by the fact that they contain, as an active component, di($\beta$-hydroxyethyl)-sulfoxide.

Di($\beta$-hydroxyethyl) sulfoxide can be prepared in accordance with the method described in French Patent 73.37867 but it is advantageously prepared by oxidizing with $H_2O_2$ the corresponding sulfide in an aqueous medium and in the presence of a small amount of a lower organic acid and preferably formic acid at a temperature of 50° to 70° C.

This process avoids the esterification of the alcohol functions of the initial reactant 2,2'-thiol diethanol, and permits the recovery of the crystallized expected product after evaporation of the water and organic acid.

In the compositions of the invention, the amount of di($\beta$-hydroxyethyl)sulfoxide can vary generally from 0.05 to 10 percent and preferably from 0.1 to 3 percent by weight, relative to the total weight of the composition.

In the compositions of the invention, the active component is combined with known cosmetic vehicles or supports.

Representative liquid vehicles, include in particular, water, aliphatic alcohols having 1-4 carbon atoms, or mixtures thereof. Representative aliphatic alcohols include more particularly alkanols having 1-4 carbon atoms and in particular ethanol or isopropyl alcohol.

When the liquid vehicle comprises a hydroalcoholic mixture, the alcohol is present in an amount up to 70 weight percent, relative to the total weight of the composition.

Such liquid vehicles, optionally in combination with other cosmetic adjuvants, provide the compositions of the present invention in the form of lotions, emulsions, gels or even in the form of pressurized compositions for aerosols, sprays or foams.

The active component can also be combined with a solid adjuvant in the form of a powder, such as for example, starch, the combination optionally being combined with a liquid propellant in pressurized compositions for dry sprays.

The cosmetic compositions of the present invention can contain in addition at least one other active component known as an agent for combatting the oily appearance of the hair and/or skin.

Among these known active components which can be used in combination with di($\beta$-hydroxyethyl)sulfoxide, are the oxathiazinone derivatives described in French Patent Application 84.07227 (Publication No. 2.545.720) having the following formula:

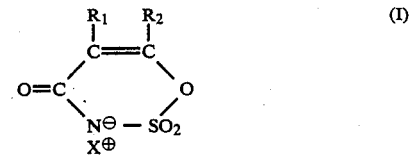

wherein $R_1$ represents hydrogen, alkyl having 1-4 carbon atoms, aryl having up to 10 carbon atoms or acyl having the formula $R_3CO$ wherein $R_3$ is alkyl having 2-4 carbon atoms;

$R_2$ represents alkyl having 1-4 carbon atoms or aryl having up to 10 carbon atoms;

or $R_1$ and $R_2$ together form, with the carbon atoms to which they are attached, an alicyclic group having up to 10 carbon atoms, optionally substituted by one or more hydrocarbon radicals;

X represents an alkali metal and preferably potassium, and more particularly the potassium salt of 3,4-dihydro-6-methyl-1,2,3-oxathiazin-4-one-2,2-dioxide (Formula I wherein $R_2$=methyl, $R_1$=H and X=K).

The combination of the compounds of Formula I, whose activity is progressive, permits to obtain with di($\beta$-hydroxyethyl)sulfoxide, an immediate effect on the oily appearance of the hair and skin, that is to say a perceptible effect from the first application.

When the indicated oxathiazinone derivative is present in the compositions of the present invention, its concentration is in the order of 0.05 to 10 percent and preferably from 0.3 to 5 percent by weight, relative to the total weight of the composition.

When the compositions according to the present invention are intended for the treatment of the hair, they can be provided principally in the form of shampoos, rinse lotions, creams, forming lotions such as hair styling lotions, brushing lotions, or in the form of aerosol compositions (foams or sprays).

When the capillary compositions according to the invention are provided in the form of a shampoo, they also contain one or more surfactants. These surfactants are selected from anionic, nonionic, cationic and amphoteric surfactants, and mixtures thereof.

In these shampoo compositions, the concentration of the surfactant generally ranges from 3 to 50 percent by weight, and preferably from 3 to 20 weight percent based on the total weight of the composition. The pH generally ranges from 3 to 10.

When the capillary compositions according to the present invention are rinse lotions, they can be provided in the form of aqueous or hydroalcoholic solutions, emulsions, thickened lotions or gels.

When the compositions of the present invention are provided in the form of emulsions, they can contain nonionic or anionic emulsifying agents.

The nonionic emulsifying agents comprise principally mixtures of oils and/or fatty alcohols or polyethoxylated alcohols such as polyethoxylated stearyl or cetylstearyl alcohols.

The anionic emulsifying agents are essentially soaps.

When the said compositions are provided in the form of thickened lotions or gels, they contain thickening agents in the presence or not of solvents.

The useful thickening agents can be sodium alginate, gum arabic, xanthane gum, or cellulose derivatives such as methyl cellulose, hydroxymethyl cellulose, hydroxyethyl cellulose, hydroxyl propyl cellulose, hydroxypropylmethyl cellulose or carboxymethyl cellulose.

The concentration of the thickening agent can range from 0.1 to 10 weight percent and, preferably, from 0.2 to 2 weight percent based on the total weight of the composition. The pH of the said rinse lotions ranges generally from 3 to 9 and preferably from 4.5 to 7.5.

When the capillary compositions according to the present invention are provided in the form of styling lotions, setting lotions, forming lotions, brushing lotions or lacquers, these lotions generally comprise an aqueous, alcohol or hydroalcoholic solution the di($\beta$-hydroxyethyl)sulfoxide, optionally in combination with at least one conventional film forming cosmetic polymer.

Representative useful film forming polymers include in particular: polyvinylpyrrolidone, copolymers of polyvinyl pyrrolidone and vinylacetate, copolymers of vinylacetate and an unsaturated carboxylic acid such as crotonic acid, the copolymers resulting from the polymerization of vinyl acetate, crotonic acid and an acrylic or methacrylic ester, the copolymers resulting from the copolymerization of vinyl acetate and an alkylvinyl ether, and the copolymers resulting from the copolymerization of vinyl acetate, crotonic acid and a vinyl ester of a long chain carbon acid.

The concentration of these polymers can range from 0.1 to 5 weight percent relative to the total weight of the composition.

One preferred form of the capillary composition according to the invention is a composition comprising an aqueous or hydroalcoholic non-rinse lotion containing 0 to 70 weight percent ethyl alcohol and including from 0.05 to 10 weight percent, preferably 0.1 to 3 weight percent of di($\beta$-hydroxyethyl)sulfoxide relative to the total weight of the composition.

According to another particularly preferred embodiment, the capillary compositon comprises an aqueous or hydroalcohol non-rinse lotion containing 0 to 70 weight percent ethylalcohol and including 0.05 to 10 weight percent and, preferably 0.1 to 3 weight percent di($\beta$-hydroxyethyl)sulfoxide, and from 0.05 to 10 weight percent and preferably 0.3 to 5 weight percent of the potassium salt of 3,4-dihydro-6-methyl-1,2,3-oxathiazin-4-one-2,2-dioxide, relative to the total weight of the composition.

These compositions can also be pressurized compositions for aerosols. There can be used as the propellant gas, $CO_2$, nitrogen, nitrous oxide, volatile hydrocarbons such as butane, isobutane, propane or, perferably chlorinated and/or fluorinated hydrocarbons.

The compositions according to the present invention can contain any other components conventionally employed in cosmetic compositions such as perfumes, dyes, preservatives, sequesterants, softening agents, synergists and/or foam stabilizers, sunscreen agents, peptizing agents and the like.

The capillary compositions according to the present invention can also be dry shampoo compositions in the form of powders or pressurized compositions for dry sprays intended for use on non-wet or non-moistened hair. After application of these dry shampoo compositions they are left on the hair for a certain period of time after which the hair is brushed.

When the cosmetic compositions of the present invention are intended to be applied to the skin, they can be provided generally in the form of emulsions such as creams or milks, gels, dermatologic cakes or aerosol foams.

These compositions can also be provided in the form of aqueous or hydroalcoholic lotions.

The hydroalcoholic lotions contain an alcohol having 1–4 carbon atoms, preferably ethanol or isopropanol, in an amount ranging from 10 to 70 weight percent based on the total weight of the composition.

These compositons for the skin can contain any adjuvant or component conventionally employed in beauty creams for the face, such as fatty bodies, emulsifiers, preservatives, perfumes, dyes, waxes and the like.

The present invention also relates to the use of di($\beta$-hydroxyethyl)sulfoxide as a cosmetic agent to improve the appearance of the skin and hair of individuals having oily skin and/or oily hair.

The present invention also relates to a cosmetic treatment process intended to improve the appearance of the skin and/or hair of persons having oily skin or oily hair, this process comprising applying a composition such as defined above on the portions of the skin, the scalp or the hair that are to be treated.

The following non-limiting examples illustrate the invention, the parts and percentages being by weight.

EXAMPLE 1

Hair lotion

A hair lotion composition is prepared by admixing the following components:

| | |
|---|---|
| di-($\beta$-hydroxyethyl) sulfoxide | 0.2 g |
| potassium salt of 3,4-dihydro- | 1.3 g |

| | |
|---|---|
| 6-methyl-1,2,3-oxathiazin-4-one 2,2-dioxide (sold under the name "ACESULFAM.K by Hoechst) | |
| ethylalcohol, sufficient amount for 20% (by volume) | |
| lactic acid, sufficient amount for pH = 4 | |
| perfume, dye, preservative, sufficient amount | |
| water, sufficient amount for | 100 g |

Applied to hair having a tendency to be oily, this lotion improves the appearance of the hair and leaves the hair supple and natural.

The di($\beta$-hydroxyethyl) sulfoxide used in this example has been prepared in the following manner:

122 g of 2,2'-thio diethanol are dissolved in 400 cm$^3$ of water and 40 cm$^3$ of formic acid.

To this mixture there are slowly added, at ambient temperature and with stirring, 109 cm$^3$ of H$_2$O$_2$ at 30%. The reaction is exothermic and the rate of introduction is regulated in a fashion such that the reaction temperature is maintained between 50° and 60° C. At the end of the introduction the reaction mixture is brought to a temperature between 65° and 70° C. for three hours.

After verifying the absence of residual peroxides, the reaction mixture is concentrated under reduced pressure. When the formic acid and the major portion of the water are evaporated, the sulfoxide crystallizes. It is then recrystallized in 500 cm$^3$ of acetone.

The crystals are filtered, washed twice with 100 cm$^3$ of acetone and dried, yielding 105 g of di($\beta$-hydroxyethyl)sulfoxide in the form of white crystals melting at 111° C.

| Elemental analysis: C$_4$H$_{10}$O$_3$S | | | | |
|---|---|---|---|---|
| | C | H | O | S |
| Calculated: | 34.76 | 7.29 | 34.75 | 23.20 |
| Found: | 34.52 | 7.31 | 34.68 | 22.96 |

EXAMPLE 2

Lotion

A lotion is prepared having the following composition: t,111

| | |
|---|---|
| di($\beta$-hydroxyethyl)sulfoxide | 0.7 g |
| 2-amino-2-methyl-1-propanol amount sufficient for pH = 6 | |
| perfume, dye, preservative, sufficient amount | |
| water, amount sufficient for | 100 g |

When applied to oily hair, this lotion improves the appearance of the hair and leaves the hair supple and natural.

EXAMPLE 3

Shampoo composition

A shampoo is prepared having the following composition:

| | |
|---|---|
| C$_{12}$-C$_{14}$ alkyl sulfate of triethanolamine | 8.0 g* |
| C$_{12}$-C$_{14}$ alkyl ether sulfate | 2.0 g* |
| of sodium, oxyethylenated with 2.2 moles of ethylene oxide | |
| hydroxyethyl cellulose, sold under the name "Natrosol 250 NHR", by Hercules | 0.5 g |
| di($\beta$-hydroxyethyl)sulfoxide | 2.0 g |
| dye, preservative - sufficient amount | |
| HCl, sufficient amount for pH = 6 | |
| water, sufficient amount for | 100.0 g |

*active material

EXAMPLE 4

Shampoo composition
The following shampoo composition was prepared:

| | |
|---|---|
| non-ionic surfactant obtained in accordance with French Patent 71.17206 by the condensation of 3.5 moles of glycidol on a C$_{11}$-C$_{14}$ alphadiol | 12.0 g |
| di($\beta$-hydroxyethyl)sulfoxide | 5.0 g |
| preservative, perfume, dye sufficient amount | |
| HCl, sufficient amount for pH = 3 | |
| water, sufficient amount for | 100.0 g |

EXAMPLE 5

Shampoo composition
The following shampoo composition was prepared:

| | |
|---|---|
| lauryl alcohol polyethoxylated with 12 moles of ethylene oxide | 8.0 g* |
| non-ionic surfactant having the formula, C$_{12}$H$_{25}$O—[C$_2$H$_3$(CH$_2$OH)O]n-H in accordance with French Patent No. 1,477,048, wherein n represents a statistical average value of about 4.2 | 3.0 g* |
| Heteropolysaccharide, sold under the name "Rhodopol 23 SC" by Rhone Poulenc | 0.5 g |
| di($\beta$-hydroxyethyl)sulfoxide | 3.0 g |
| preservative, dye, sufficient amount | |
| triethanolamine, sufficient for pH = 8 | |
| water, sufficient amount for | 100.0 g |

*active material

EXAMPLE 6

Lotion
The following lotion was prepared:

| | |
|---|---|
| di($\beta$-hydroxyethyl)sulfoxide | 2.0 g |
| perfume, dye, preservative sufficient amount | |
| water, sufficient amount for spontaneous pH = 7. | 100.0 g |

What is claimed is:

1. A process for improving the appearance of the hair or skin of persons having oily hair or oily skin comprising applying to said oily hair or oily skin, in an amount effective to improve the appearance thereof, a cosmetic composition comprising in a cosmetically acceptable vehicle an amount of di($\beta$-hydroxyethyl) sulfoxide effective to combat the oily appearance of the hair or skin.

* * * * *